(12) United States Patent
Beumer et al.

(10) Patent No.: US 9,468,594 B2
(45) Date of Patent: Oct. 18, 2016

(54) FLAVOR AND FRAGRANCE FORMULATION (II)

(71) Applicant: DSM IP ASSETS B.V., Heerlen (NL)

(72) Inventors: Raphael Beumer, Basel (CH); Johannes Tschumi, Basel (CH); Michael Gressly, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/430,345

(22) PCT Filed: Oct. 7, 2013

(86) PCT No.: PCT/EP2013/070830
§ 371 (c)(1),
(2) Date: Mar. 23, 2015

(87) PCT Pub. No.: WO2014/056847
PCT Pub. Date: Apr. 17, 2014

(65) Prior Publication Data
US 2015/0245985 A1    Sep. 3, 2015

(30) Foreign Application Priority Data
Oct. 8, 2012 (EP) .................................. 12187641

(51) Int. Cl.
| | |
|---|---|
| C08F 2/46 | (2006.01) |
| C08F 2/50 | (2006.01) |
| C08G 61/04 | (2006.01) |
| A61K 8/00 | (2006.01) |
| A61K 8/35 | (2006.01) |
| A23L 1/226 | (2006.01) |
| A61Q 13/00 | (2006.01) |
| C07C 49/175 | (2006.01) |
| C11B 9/00 | (2006.01) |
| C11D 3/50 | (2006.01) |
| A61Q 19/00 | (2006.01) |
| A61L 9/01 | (2006.01) |
| A61Q 5/02 | (2006.01) |
| A61Q 15/00 | (2006.01) |
| A61Q 19/10 | (2006.01) |
| C07C 49/04 | (2006.01) |
| C07C 49/203 | (2006.01) |
| C11D 3/20 | (2006.01) |

(52) U.S. Cl.
CPC .............. *A61K 8/35* (2013.01); *A23L 1/22628* (2013.01); *A61L 9/01* (2013.01); *A61Q 5/02* (2013.01); *A61Q 13/00* (2013.01); *A61Q 15/00* (2013.01); *A61Q 19/00* (2013.01); *A61Q 19/10* (2013.01); *C07C 49/04* (2013.01); *C07C 49/175* (2013.01); *C07C 49/203* (2013.01); *C11B 9/0015* (2013.01); *C11D 3/2072* (2013.01); *C11D 3/50* (2013.01); *A61K 2800/10* (2013.01)

(58) Field of Classification Search
CPC .... A61K 8/35; A61K 2800/10; C07C 49/04; C07C 49/175; C07C 49/203; A61Q 13/00; A61Q 5/02; A61Q 15/00; A61Q 19/10; A61Q 19/00; C11D 3/2072; C11D 3/50; A61L 9/01; C11B 9/0015; A23L 1/22628
USPC ............. 522/27, 7, 6, 71, 189, 184, 1; 512/1
See application file for complete search history.

(56) References Cited

U.S. PATENT DOCUMENTS 2,815,379 A * 12/1957 Surmatis ................ C07C 45/292
512/22
2,824,896 A * 2/1958 Surmatis ................. C07C 29/42
512/25

FOREIGN PATENT DOCUMENTS

| GB | 785 086 | 10/1957 |
|---|---|---|
| GB | 785086 | * 10/1957 |
| WO | WO 02/051453 | 7/2002 |

OTHER PUBLICATIONS

Misharnina et al, Formation and Flavor of dry Champignons, 2010, Prikladnaya Biokhimiya i Mikrobiologiya, vol. 46, No. 1, 119-124.*
International Search Report for PCT/EP2013/070830, mailed Jan. 17, 2014, 6 pages.
Written Opinion of the International Searching Authority for PCT/EP2013/070830, mailed Jan. 17, 2014, 5 pages.

* cited by examiner

*Primary Examiner* — Ling Choi
*Assistant Examiner* — Jessica E Whiteley
(74) *Attorney, Agent, or Firm* — Nixon & Vanderhye P.C.

(57) ABSTRACT

The present invention relates to the use of specific organic compounds as flavor and fragrance material. Furthermore the invention relates to a new specific organic compound, as well as to flavor and fragrance formulations comprising at least one of the specific organic compounds.

8 Claims, No Drawings

FLAVOR AND FRAGRANCE FORMULATION (II)

This application is the U.S. national phase of International Application No. PCT/EP2013/070830, filed 7 Oct. 2013, which designated the U.S. and claims priority to EP Application No. 12187641.1, filed 8 Oct. 2012, the entire contents of each of which are hereby incorporated by reference.

The present invention relates to the use of specific organic compounds as flavor and fragrance material. Furthermore the invention relates to new specific organic compounds, as well as to flavor and fragrance formulations comprising at least one of the specific organic compounds.

In the flavor and fragrance industry there is always a need and demand for compounds that enhance, modify, improve or otherwise positively influence an odour note and therefore giving perfumers or other persons the ability to create new fragrances for perfumes, colognes, personal care products, household products or any other products, which comprise flavor and fragrance materials.

Surprisingly it was found that the compounds of formula (I) and/or compounds of formula (II) are very useful as flavor and fragrance material.

Therefore the present invention is related to the use of a compound of formula (I) and/or a compound of formula (II)

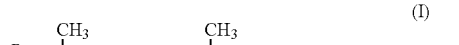
(I)

(II)

wherein
$R_1$ signifies $-CH_3$, $-CH_2CH_3$ or $-CH_2CH_2CH_3$, and
$R_2$ signifies $-H$ or $-CH_3$, and
$R_3$ signifies $-H$ or $-OCH_3$, and
$R_4$ signifies $-CH_2CH_3$ or $-CH_2CH_2CH_3$, and
$R_5$ signifies $-H$ or $-CH_3$,
as flavor and fragrance material.

Preferred is the use of at least one compound selected from the group consisting of the compounds of formulae (Ia)-(Ig) and of the compounds of formulae (IIa)-(IId) and any of the mixtures of compounds of formulae (Ia)-(Ig) and compounds of formulae (IIa)-(IId):

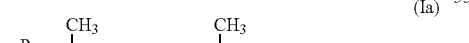
(Ia)

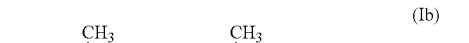
(Ib)

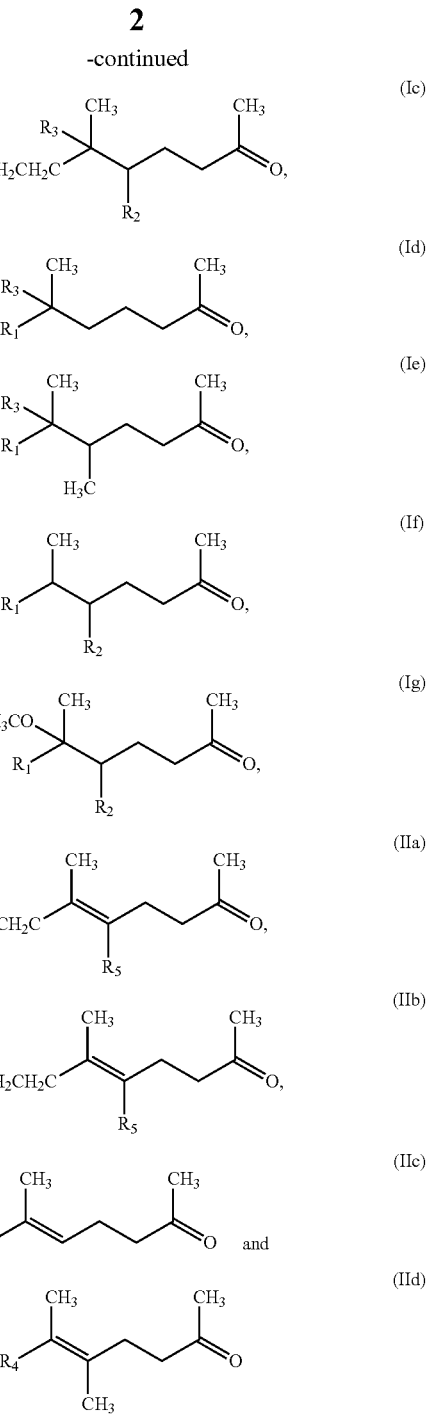

wherein $R_1$, $R_2$, $R_3$, $R_4$ and $R_5$ have the same meanings as defined above, as flavor and fragrance material.

More preferred is the use of at least one compound selected from the group consisting of compounds of formulae (III)-(X) and any of their mixtures

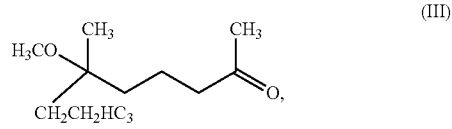
(III)

-continued

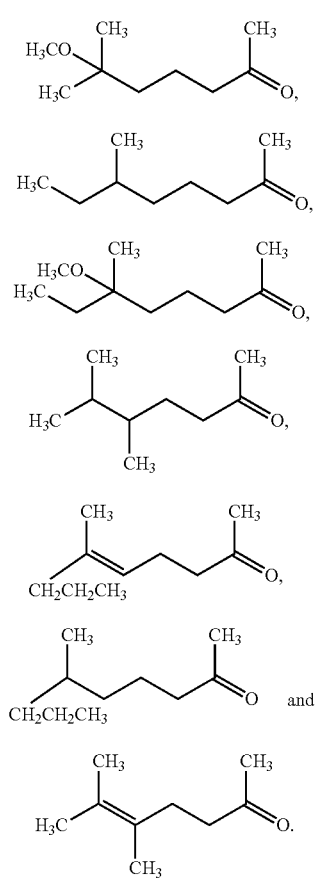

(IV), (V), (VI), (VII), (VIII), (IX), (X)

The compounds of formula (I) and/or compounds of formula (II) may be used as such or in combination with other compounds of formula (I) and/or compounds of formula (II) or other compounds which are known as flavor and fragrance material.

Such other compounds which are known as flavor and fragrance material include all known odorant molecules selected from the extensive range of natural products and synthetic molecules currently available, such as essential oils, alcohols, aldehydes and ketones, ethers and acetals, esters and lactones, macrocycles and heterocycles, and/or in admixture with one or more ingredients or excipients conventionally used in conjunction with odorants in flavor fragrance formulations, for example, carrier materials, and other auxiliary agents commonly used in the art.

The flavor and fragrance material of the present invention is used in a flavor and fragrance formulation.

Such a flavor and fragrance formulation comprises other ingredients.

The flavor and fragrance formulation according to the present invention can be in any form. Usually it is in a solid, gel-like or liquid (or a combination thereof) form.

It can also be in an encapsulated form (i.e. a liquid formulation encapsulated by a suitable matrix material).

Therefore the present invention also relates to flavor and fragrance formulations comprising at least one compound of formula (I) and/or at least one compound of formula (II)

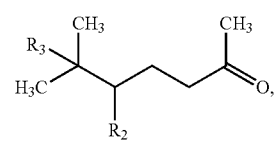

(I)

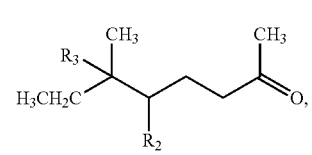

(II)

wherein $R_1$ signifies —$CH_3$, —$CH_2CH_3$ or —$CH_2CH_2CH_3$, and $R_2$ signifies —H or —$CH_3$, and $R_3$ signifies —H or —$OCH_3$, and $R_4$ signifies —$CH_2CH_3$ or —$CH_2CH_2CH_3$, and $R_5$ signifies —H or —CH.

Preferred are flavor and fragrance formulations comprising at least one compound selected from the group consisting of the compounds of formulae (Ia)(Ig) and of the compounds of formulae (IIa)-(IId), as well as any of the mixtures of compounds of formulae (Ia)-(Ig) and (IIa)-(IId):

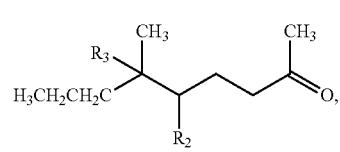

(Ia)

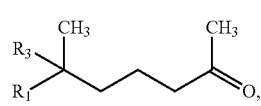

(Ib)

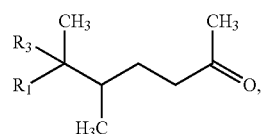

(Ic)

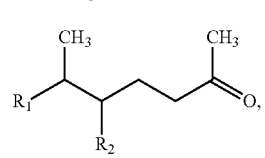

(Id), (Ie), (If)

-continued

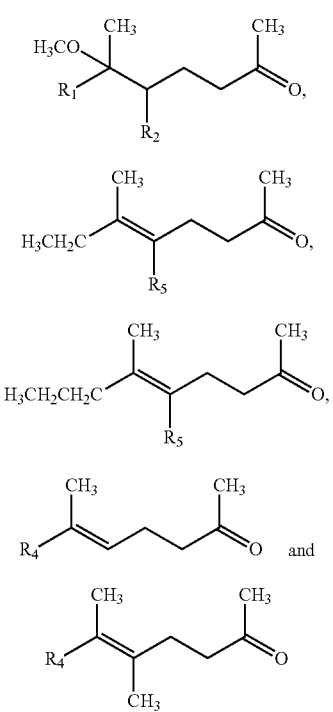

wherein $R_1$, $R_2$, $R_3$, $R_4$ and $R_5$ have the same meanings as defined above.

More preferred are flavor and fragrance formulations comprising at least one compound selected from the group consisting of compounds of formulae (III)(X) and any of their mixtures

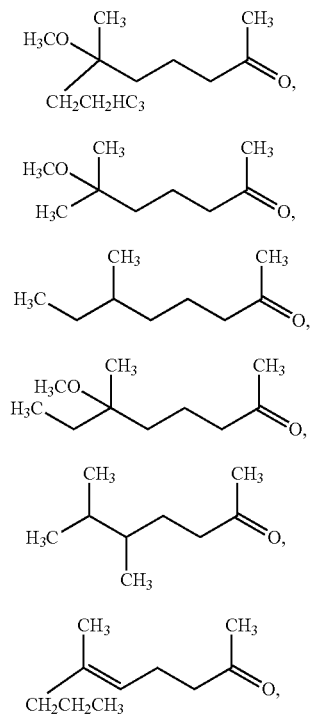

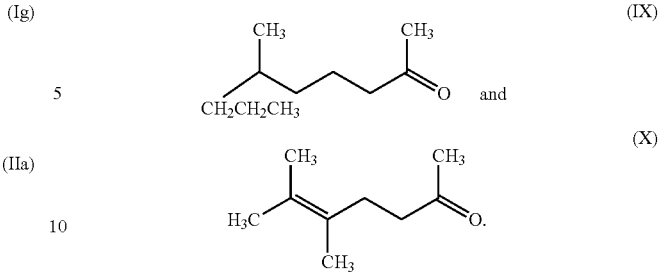

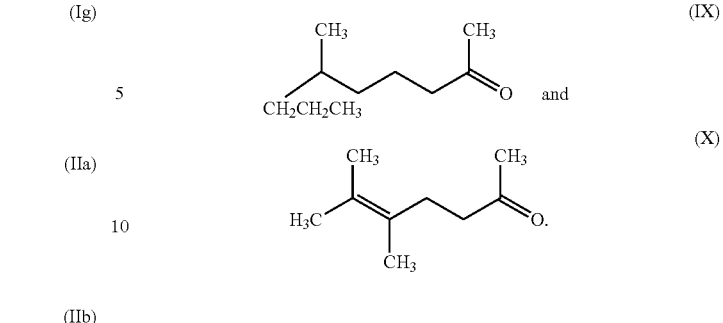

When a compound of formula (I) and/or compound of formula (II) is used in a flavor and fragrance formulation, then the amount thereof is in the range of 0.0001-10 weight-% (wt-%), related to the total weight of the flavor and fragrance formulation. Preferred is an amount in the range of 0.01-5 wt-%, based on the total weight of the flavor and fragrance formulation.

Therefore the present invention relates to liquid flavor and fragrance formulations comprising
(i) 0.0001-10 wt-% (preferably 0.01-5 wt-%), related to the total weight of the flavor and fragrance formulation, of at least one compound of formula (I) and/or of at least one compound of formula (II).

Therefore the present invention relates to preferred liquid flavor and fragrance formulations comprising
(i) 0.0001-10 wt-% (preferably 0.01-5 wt-%), related to the total weight of the flavor and fragrance formulation, of at least one compound of formula chosen from the group consisting of the compounds of formula (Ia)-(Ig) and (IIa)-(IId).

Therefore the present invention relates to more preferred liquid flavor and fragrance formulations comprising
(i) 0.0001-10 wt-% (preferably 0.01-5 wt-%), related to the total weight of the flavor and fragrance formulation, of at least one compound of formula chosen from the group consisting of the compounds of formula (III)-(X).

The flavor and fragrance formulations according to the present invention can comprise further ingredients (=auxiliary compounds), such as any further perfuming compounds solvents, adjuvants, thickeners, surface active agents, pigments, extenders, rheology modifiers, dyestuffs, antioxidants, fillers and the like.

Many flavor and fragrance formulations are in a liquid form (like a perfume, cologne, etc.). Therefore, for such a liquid formulation a (diluent) solvent is present. Such common diluents are i.e. dipropyleneglycol, isopropylmyristate, triethylcitrate and alcohols (such as ethanol).

Further examples of fine perfumery are Eau de perfume, Eau de Toilette, Eau de Cologne and Splash Cologne. Fine perfumery products are commonly based on an alcoholic solution as diluent. However fine perfumery products using an oil or wax as diluent are also included within the meaning of this invention. The compounds can be employed in widely varying amounts, depending upon the specific application and on the nature and quantity of other odorant ingredients. When used in a (fine) perfume, the amount is usually between 0.01-10 wt-%, based on the total weight of the (fine) perfume.

However, these values and ranges are given only by way of example, since the experienced perfumer may also achieve effects or may create novel accords with lower or higher concentrations.

Furthermore the present invention relates to liquid flavor and fragrance formulations comprising
  (i) at least one compound of formula (I) and/or at least one compound of formula (II), and
  (ii) at least one diluent chosen from the group consisting of dipropyleneglycol, isopropylmyristate, triethylcitrate and alcohols (such as ethanol), and optionally
  (iii) at least one auxiliary compound selected from the group consisting of perfuming compounds solvents, adjuvants, thickeners, surface active agents, pigments, extenders, rheology modifiers, dyestuffs, antioxidants and fillers.

Furthermore the present invention relates to preferred liquid flavor and fragrance formulations comprising
  (i) at least one compound of formula chosen from the group consisting of the compounds of formula (Ia)-(Ig) and (IIa)-(IId), and
  (ii) at least one diluent chosen from the group consisting of dipropyleneglycol, isopropylmyristate, triethylcitrate and alcohols (such as ethanol), and optionally
  (iii) at least one auxiliary compound selected from the group consisting of perfuming compounds solvents, adjuvants, thickeners, surface active agents, pigments, extenders, rheology modifiers, dyestuffs, antioxidants and fillers.

Furthermore the present invention relates to more preferred liquid flavor and fragrance formulations comprising
  (i) at least one compound of formula chosen from the group consisting of the compounds of formula (III)-(X), and
  (ii) at least one diluent chosen from the group consisting of dipropyleneglycol, isopropylmyristate, triethylcitrate and alcohols (such as ethanol), and optionally
  (iii) at least one auxiliary compound selected from the group consisting of perfuming compounds solvents, adjuvants, thickeners, surface active agents, pigments, extenders, rheology modifiers, dyestuffs, antioxidants and fillers.

Furthermore the present invention relates to solid flavor and fragrance formulations comprising
  (i) at least one compound of formula (I) and/or at least one compound of formula (II), and
  (ii) at least one auxiliary compound selected from the group consisting of perfuming compounds solvents, adjuvants, thickeners, surface active agents, pigments, extenders, rheology modifiers, dyestuffs, antioxidants and fillers.

Furthermore the present invention relates to preferred solid flavor and fragrance formulations comprising
  (i) at least one compound of formula chosen from the group consisting of the compounds of formula (Ia)-(Ig) and (IIa)-(IId), and
  (ii) at least one auxiliary compound selected from the group consisting of perfuming compounds solvents, adjuvants, thickeners, surface active agents, pigments, extenders, rheology modifiers, dyestuffs, antioxidants and fillers.

Furthermore the present invention relates to more preferred solid flavor and fragrance formulations comprising
  (i) at least one compound of formula chosen from the group consisting of the compounds of formula (III)-(X), and
  (ii) at least one auxiliary compound selected from the group consisting of perfuming compounds solvents, adjuvants, thickeners, surface active agents, pigments, extenders, rheology modifiers, dyestuffs, antioxidants and fillers.

The compounds of formula (I) and the compounds of formula (II) may be used in a broad range of flavor and fragrance formulations, e.g. in any field of fine and functional perfumery, such as perfumes, air care products, household products, laundry products, body care products and cosmetics.

The compounds as described hereinabove may be employed in a flavor and fragrance formulation simply by directly mixing at least one compound of formula (I) and/or at least one compound of formula (II), a mixture thereof, or a fragrance composition with the other ingredients used in the final product, or they may, in an earlier step, be entrapped with an entrapment material, for example, polymers, capsules, microcapsules and nanocapsules, liposomes, film formers, absorbents such as carbon or zeolites, cyclic oligosaccharides and mixtures thereof, or they may be chemically bonded to substrates, which are adapted to release the fragrance molecule upon application of an external stimulus such as light, enzyme, or the like, and then mixed with the other ingredients used in the final product.

Thus, the invention additionally provides a method of manufacturing a flavor and fragrance formulation, comprising the incorporation of at least one compound of formula (I) and/or at least one compound of formula (II), as a fragrance ingredient, either by directly admixing the compound to the other ingredients used in the final product or by admixing a fragrance composition comprising at least one compound of formula (I) and/or at least one compound of formula (II), which may then be mixed with the other ingredients used in the final product, using conventional techniques and methods.

Thus, the invention additionally provides a preferred method of manufacturing a flavor and fragrance formulation, comprising the incorporation of at least one compound of formula chosen from the group consisting of the compounds of formula (Ia)-(Ig) and (IIa)-(IId), as a fragrance ingredient, either by directly admixing the compound to the other ingredients used in the final product or by admixing a fragrance composition comprising at least one compound of formula chosen from the group consisting of the compounds of formula (Ia)-(Ig) and (IIa)-(IId), which may then be mixed with the other ingredients used in the final product, using conventional techniques and methods.

Thus, the invention additionally provides a more preferred method of manufacturing a flavor and fragrance formulation, comprising the incorporation of at least one compound of formula chosen from the group consisting of the compounds of formula (III)-(X), as a fragrance ingredient, either by directly admixing the compound to the other ingredients used in the final product or by admixing a fragrance composition comprising at least one compound of formula chosen from the group consisting of the compounds of formula (III)-(X), which may then be mixed with the other ingredients used in the final product, using conventional techniques and methods.

Through the addition of an olfactory acceptable amount of a compound of the present invention as hereinabove described, or a mixture thereof, the odor notes of a consumer product base will be improved, enhanced or modified. Thus, the invention furthermore provides a method for improving, enhancing or modifying a consumer product (=final product) base by means of the addition thereto of an olfactory acceptable amount of at least one compound of formula (I) and/or at least one compound of formula (II).

Thus, the invention furthermore provides a preferred method for improving, enhancing or modifying a consumer product (=final product) base by means of the addition thereto of an olfactory acceptable amount of at least one compound of formula chosen from the group consisting of the compounds of formula (Ia)-(Ig) and (IIa)-(IId).

Thus, the invention furthermore provides a more preferred method for improving, enhancing or modifying a consumer product (=final product) base by means of the addition thereto of an olfactory acceptable amount of at least one compound of formula chosen from the group consisting of the compounds of formula (III)-(X).

In the context of the present invention the olfactory effective amount is to be understood as the amount of the at least one compound of formula (I) and/or of the at least one compound of formula (II) in a flavor and fragrance formulation will contribute to its particular olfactory characteristics, but the olfactory effect of the flavor and fragrance formulation will be the sum of the effects of each of the perfumes or fragrance ingredients. Thus the compounds of the invention can be used to alter the aroma characteristics of the flavor and fragrance formulation, or by modifying the olfactory reaction contributed by another ingredient in the composition. The amount will vary depending on many factors including other ingredients, their relative amounts and the effect that is desired.

As used herein, "consumer product (=final product)" means a composition for use as a consumer product to fulfill specific actions, such as cleaning, softening, and caring or the like. Examples of such products include fine perfumery, e.g. perfume and eau de toilette; fabric care; household products and personal care products such as laundry care detergents, rinse conditioner, personal cleansing composition, detergent for dishwasher, surface cleaner; laundry products, e.g. softener, bleach, detergent; body care products, e.g. shampoo, shower gel; air care products and cosmetics, e.g. deodorant, vanishing creme. This list of products is given by way of illustration and is not to be regarded as being in any way limiting.

The compounds of formula (I) and the compounds of formula (II) may be prepared using methods known to the person skilled in the art of organic synthesis.

Furthermore the present invention relates to the following compound of formula (III) which is a novel compound

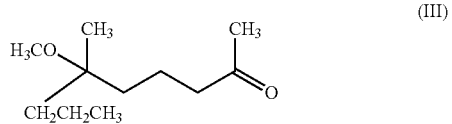

(III)

and may be prepared by methoxylation of 6-methyl-5-nonen-2-on.

The invention is now further illustrated in the following non-limiting examples.

EXAMPLES

All compounds were evaluated by a panel of four persons for their intensity whereby a range of 1 to 10 was used (1=very low intensity; 10=very high intensity). Furthermore these four persons also described the odor of the compounds. The tenancy was evaluated by one person after 3, 6, 8, 24, 48, 72 and 96 hours. For such evaluations a piece of paper was immersed in each single liquid compound as such.

Example 1

Manufacture and Olfactory Properties of the Compound of Formula III a) Manufacture of 6-methoxy-6-methyl-nonan-2-on (compound of formula III) by methoxylation of 6-methyl-5-nonen-2-on 6404.0 g of 6-methyl-5-nonen-2-on, 10400.0 g of methanol and 2050.0 g of Amberlyst 15 wet are mixed in a reactor and heated up to 80° C. After 15 hours the reaction mixture is cooled and reduced in volume by distilling. The remaining residue is then distilled (2 mbar; 145° C.) to give 6-methoxy-6-methyl-nonan-2-on.

b) Olfactory Properties

Odor description: wood; wood treating agent; empty tobacco pipe.
Intensity: 7.5.
Tenancy: 8-24 hours.

Example 2

Olfactory Properties of the Compound of Formula IV

Odor description: good—not too strong; mild; camphor; Dulix; a bit sweet; fresh; menthol; peppermint.
Intensity: 7.
Tenancy: 3-6 hours.

Example 3

Olfactory Properties of the Compound of Formula V

Odor description: fruity; water melon; flowers; leek/field garlic; seeds of herbs.
Intensity: 7.5.
Tenancy: 3-6 hours.

Example 4

Olfactory Properties of the Compound of Formula VI

Odor description: weakly etherial; woody; fir needles; fresh; herbs; menthol.
Intensity: 5.
Tenancy: 3-6 hours.

Example 5

Olfactory Properties of the Compound of Formula VII

Odor description: similar to 6-methyl-5-hepten-2-on, but fresher; tropical fruits;
warm wood; a bit mint.
Intensity: 7.5.
Tenancy: 0-3 hours.

Example 6

Olfactory Properties of the Compound of Formula VIII

Odour description: apple; granny Smith.
Intensity: 6.5.
Tenancy: 3-6 hours.

Example 7

Olfactory Properties of the Compound of Formula IX

Odor description: fresh clothes; sweet; warm; herb; tropical fruit.
Intensity: 7.
Tenancy: 3-6 hours.

Example 8

Olfactory Properties of the Compound of Formula X

Odor description: ketone like; sweet; dirty.
Intensity: 6.5.
Tenancy: 3-6 hours.

The invention claimed is:
1. A compound of formula (III):

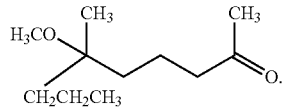

2. A flavor and fragrance formulation comprising the compound according to claim 1.
3. The flavor and fragrance formulation according to claim 2, which further comprises at least one compound of formula (II):

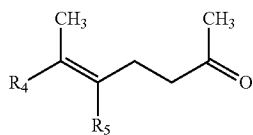

wherein $R_4$ signifies —$CH_2CH_3$ or —$CH_2CH_2CH_3$, and $R_5$ signifies —H or —$CH_3$.

4. The flavor and fragrance formulation according to claim 2, wherein the compound of formula (III) is present in an amount of 0.0001-10 wt-%, relative to the total weight of the flavor and fragrance formulation.
5. The flavor and fragrance formulation according to claim 2, wherein the flavor and fragrance formulation is solid, gel or liquid.
6. The flavor and fragrance formulation according to claim 2, wherein the flavor and fragrance formulation is a perfume, air care product, household product, laundry product, body care product or cosmetic product.
7. A method of improving, enhancing or modifying a flavor and fragrance formulation which comprises adding to the flavor and fragrance formulation an olfactory acceptable amount of the compound according to claim 1.
8. The method according to claim 7, which further comprises further adding to the flavor and fragrance formulation at least one compound of formula (II):

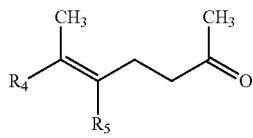

wherein $R_4$ signifies —$CH_2CH_3$ or —$CH_2CH_2CH_3$, and $R_5$ signifies —H or —$CH_3$.

* * * * *